United States Patent [19]

Rips et al.

[11] 4,297,346
[45] Oct. 27, 1981

[54] PSEUDOPEPTIDES USED AS MEDICAMENTS

[75] Inventors: Richard Rips; Elisabeth Morier, both of Paris, France

[73] Assignee: Institut National de la Sante et de la Recherche Medicale, Paris, France

[21] Appl. No.: 101,555

[22] Filed: Dec. 7, 1979

Related U.S. Application Data

[63] Continuation of Ser. No. 14,314, Feb. 23, 1979, abandoned, which is a continuation of Ser. No. 858,479, Dec. 8, 1977, abandoned.

[30] Foreign Application Priority Data

Dec. 10, 1976 [GB] United Kingdom ............... 51632/76

[51] Int. Cl.$^3$ .................... A61K 37/00; C07C 103/52; C07G 7/00
[52] U.S. Cl. .............................. 424/177; 260/112.5 R
[58] Field of Search ..................... 260/112.5 R, 112 S, 260/112 TR, 112 LH; 424/177

[56] References Cited

U.S. PATENT DOCUMENTS

| 3,429,869 | 2/1969 | Salat et al. | 260/112.5 R |
|---|---|---|---|
| 3,843,447 | 10/1974 | Burkoth | 260/112.5 R |
| 3,878,187 | 4/1975 | Schneider et al. | 260/112.5 R |
| 3,998,799 | 12/1976 | Boder et al. | 260/112.5 R |
| 4,043,989 | 8/1977 | Schneider et al. | 260/112.5 R |
| 4,064,235 | 12/1977 | Yanihara et al. | 260/112.5 R |
| 4,064,236 | 12/1977 | Dorn | 260/112.5 R |

Primary Examiner—Delbert R. Phillips
Assistant Examiner—Blondel Hazel
Attorney, Agent, or Firm—Dressler, Goldsmith, Shore, Sutker & Milnamow, Ltd.

[57] ABSTRACT

The invention relates to therapeutic agents referred to as 'pseudopeptides' being formed from at least one peptide radical connected by a peptide bond to a therapeutically active molecule or derivative of a therapeutically active molecule. The therapeutic agents of the invention may be in the form of derivatives such as salts, esters and amides. The basis of action of the agents of the invention is the ability of the agents of the invention to cross bodily biological barriers because of the basically peptide structure of the agents. The invention also includes the preparation of the agents of the invention.

15 Claims, No Drawings

PSEUDOPEPTIDES USED AS MEDICAMENTS

This is a continuation of application Ser. No. 014,314, filed Feb. 23, 1979, now abandoned, which in turn is a continuation of application Ser. No. 858,479, now abandoned, filed Dec. 8, 1977 now abandoned.

The present invention is concerned with a new type of medicament which is called a "pseudopeptide".

Although it has to be considered that the first peptidic synthesis dates from 1901, it was necessary to wait fifty years before Vincent du Vigneaud and his team obtained, by synthesis, peptides secreted by posthypophysis, the character of which had been suspected since 1924. Initially used as structural evidence of natural products by several specialised laboratories, the peptidic synthesis was then extended to research in connection with antihormones, and then came into general use for reaching the present state, in which, for example, peptides having little relationship with neurohormones are subjected to pharmacological investigation of psychotropic subjects.

It seems that this is particularly the case from the description of the activities on the central nervous system of easily available peptides, such as the antidepressive TRH or the anti-Parkinson MIF, from which has arisen a wave of synthesis procedures by permutation of natural amino acids, this having led to a very high number of patents describing therapeutic properties.

The present invention is based on another discovery. In therapeutic chemistry, the notion of receptor has been used, since the beginning of the century, within the scope of the Ehrlich keylocking hypothesis; its representation was that of a negative of a known therapeutic efficiency structure and the use thereof was the definition of the steric and sometimes electronic limits of structural variations possible for obtaining an equal pharmacological activity with a molecule different from its model.

The results which are obtained in molecular pharmacology and biology and concerning, inter alia, the receptors of steroids and acetylcholine, lead to the idea that the majority of the receptors are macromolecules in which the medicament occupies only a small part of the whole. It is probable that these macromolecules can in addition be deformed under various influences, including that of the occupation of certain of their sites by molecules having a medicament action. It is probable that at least some of the receptors are proteic. This leads to considering the possibility of medicament-receptor correspondence being greater with a peptide than with another active molecule.

This is the reason why the present invention is concerned with a new type of medicament which is called a "pseudopeptide".

Within the present specification, it is understood that there is designated by "pseudopeptide" a chemical compound which is formed by at least one peptidic radical connected by a peptide bond to at least one radical corresponding to a molecule or a derivative of a therapeutically active molecule.

In the foregoing definition, it is essentially understood that what is designated by "radical corresponding to a therapeutically active molecule" is a radical of formula:

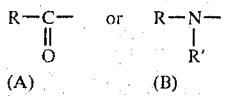

the therapeutically active molecule being RCOOH or RNHR', while what is understood by "radical corresponding to a derivative of a therapeutically active molecule" is a radical A or B, in which the therapeutically active molecule has the formula RH or substituted R in place of hydrogen, an ester of the acid

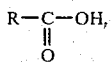

an amide of RCOOH or of RNHR', or a secondary or tertiary amine

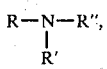

in which R' is hydrogen or a substituent different from hydrogen.

Consequently, the present invention is concerned quite generally with a pseudopeptide as a medicament.

The present invention is also concerned, as regards a medicament, with the pseudopeptides as previously defined in the form of a salt, ester or amide, particularly the pharmaceutically acceptable salt, ester and amide, as well as the pseudopeptides carrying protected functions. This is the reason why it is necessary, in the specification, when "pseudopeptides" are referred to, to understand that this term also includes the different derivatives as previously mentioned.

Because of the presence of a peptidic fraction, the pseudopeptides according to the present invention make possible the improvement in the action of the active molecule by increasing probability of this molecule reaching the corresponding proteic receptor and/or by increasing the probability of the said active molecule, in pseudopeptide form, being able to overcome certain biological barriers which normally it is unable to cross in the form of a free molecule.

What is understood by "peptide" in the present specification is essentially a linkage of ordinary amino acids which are derived from proteins, plus proline and hydroxyproline, and possibly the cyclic forms of these amino acids, when they are able to exist, as for example glutamic acid.

The present invention is more particularly concerned with pseudopeptides in which the peptidic radicals originate from peptides having an action on the nervous system, that is to say, neuropeptides which preferably have less than 12 amino acid sequences, for example, the neuropeptides:

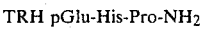

and the encephalines:

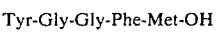

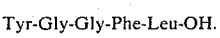

Although it is preferred, for reasons concerned with synthesi problems and preparation costs, to use short-chain peptidic radicals, this does not include the use of peptidic radicals originating from peptide, such as endorphine:

Tyr-Gly-Gly-Phe-Met-Thr-Ser-Glu-Lys-Ser-Glu-Thr-Pro-Leu-Val-Thr-OH containing 16 amino acid sequences.

The radical originating from peptides, particularly neuropeptides, may originate from the neuropeptide itself, by removal of the hydrogen from a terminal amino function, or $NH_2$ from an amide function, or of OH from a terminal acid function, but may in like manner originate from a derivative of the neuropeptide, that is to say, from a compound having the same amino acid chain as the neuropeptide, but without one or more of the terminal sequences.

Thus, the peptidic radical could be pGlu-His, originating from TRH of formula

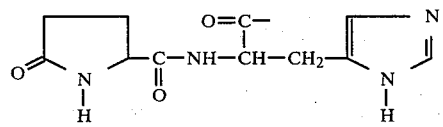

Pro-Leu, originating from MIF of formula

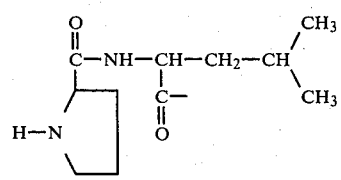

Tyr-Gly-Gly, originating from encephalines of formula

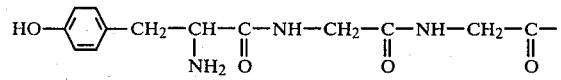

The peptidic radical of the pseudopeptides will comprise at least two amino acid sequences.

Among the active molecules, there will preferably be chosen molecules having a central or peripheral effect, acting through a central mechanism, that is to say, essentially molecules which act on the central nervous system.

Among these molecules, there may be mentioned the molecules which belong to the following therapeutic classes:
analeptic
analgesic
anaesthetic
anorexigenic
serotonin-antagonistic
anti-anginous
anti-arrythmic
anti-asthenic
anti-cholinergic
anti-cholinesterasic
anti-convulsive
anti-emetic
anti-epileptic
anti-migrainous
anti-Parkinsonian
anti-pyretic
anti-tussive
bronchodilatative
contraceptive
hypertensive
hypotensive
myoresolutive
orexigenic and more particularly the psychotropic molecules.

Among the radicals which correspond to a therapeutically active molecule, it is necessary to mention the radicals of formula

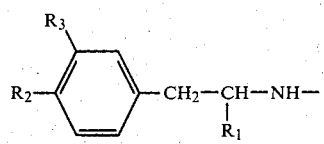

in which $R_1$ is H or $CH_3$, $R_3$ is H or OH and $R_2$ is H, OH, Cl, $NO_2$ or $NH_2$, which correspond to amphetamine or dopamine derivatives, and also the radical

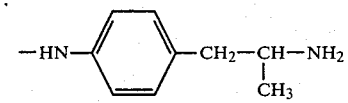

which corresponds to 4-aminoamphetamine.

Among the pseudopeptides of the present invention, it is necessary to mention more particularly pGlu-His-Amph, which is useful in the treatment of asthenia and obesity, and pGlu-His-DA, which is useful in the treatment of Parkinson's disease. Similarly, the pharmacological properties and the central action of the following active molecules is improved: phenylethylamine, the 4-chloro-amphetamines, 4-amino-amphetamines, 4-nitro-amphetamines, by administering them in the pseudopeptide form, which comprises the pGlu-His radical as peptidic fraction.

Phenylethylamine having a sympathomimetric action was found in the brain of a rat, mouse, rabbit and in a human being. Its action on the temperature is two-phase; hyperthermia followed by a long-lasting hypothermia; the same applies as regards the motive activity, where the effect as a function of time is complicated by a variation due to the dosages. The antidepressants increase its cerebral rate and it has itself an antagonistic action of the reserpine. As regards human beings, it would be responsible for the anti-depressive action of the phenylalanine and its therapeutic activity in the treatment of Parkinson's disease.

The depletive action of the cerebral indolamines and more especially of the serotonin of the 4-chloro-amphetamine, although known for more than ten years, is not explained by its structure. This latter is analogous to that of amphetamine, which effects particularly the pyrocatechol amines. Investigations carried out on homologues have made it possible to suggest in this field structure-activated relations. The comparison of the behavioural and especially biochemical activities of the pseudopeptides prepared from one or other of these amines could possibly contribute to resolving this problem.

The 4-nitro-amphetamine causes a depletion of serotonin and a decrease in the activity of the tryptophane hydroxylase in 4 hours, which is still perceptive two weeks later.

On the contrary, the 4-amino-amphetamine causes an increase in the amount of serotonin, while the activity of the tryptophane hydroxylase is not modified to any appreciable degree.

Similarly, the use of pseudopeptides comprising pGlu-His and Pro-Leu, as peptidic radical, and a radical which is derived from the following molecules:

5-(3-aminopropylidene)dibenzo-(a,d)-cyclohepta-1,4-diene (R—NH— radical) permits of obtaining an analogue of amitriptylene (formula R—N(CH$_3$)$_2$) and of nortriptyline, having an antidepressive action, 1,3-dihydro-7-amino-5-phenyl-1H-benzodiazepine-(1,4)-one(2) (R—NH—radical), permits of obtaining an analogue of chlorazepam and of nitrazepam (formula R—NO$_2$), having an anxiolytic or tranquillising activity, 3-chloro-10-(3-aminopropyl)-phenthiazine (radical R—NH—), permits of obtaining an analogue of chloropromazine (formula R—N(CH$_3$)$_2$), having a tranquillising action.

Using a pseudopeptide which comprises, as peptidic radical, the pGlu-His or Pro-Leu radical or the tyrosyl-glycyl-glycyl (Tyr-Gly-Gly) radical of the encephalines and a radical which is derived from:

4-amino-antipyrine (R—NH radical), analogue of antipyrine (formula R—H), the paraethoxy-aniline (R—NH— radical), analogue of the para-phenetidine (formula RNH$_2$), the 4-phenyl-4-ethoxycarbonyl piperidine

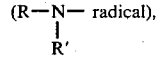

analogue of pethidine

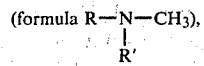

compounds having improved analgesic activities are obtained.

Compounds with an anti-epilepsy activity could be obtained by using a pseudopeptide comprising a peptidic radical of the MIF (Melanocyte inhibiting factor) and radicals which are derived from the hydantoins, barbituric acids and oxazolidines, on which will have previously been grafted amino functions.

The pseudopeptides in accordance with the present invention can be synthesised by processes which are similar to the processes which are known in connection with the synthesis of peptides, and hence it is possible to synthesise the peptidic chain, either by adding the sequences in succession, or by synthesising sequential blocks, which are then inter-condensed. It is also possible to condense the active molecule after the peptidic fraction has been synthesised or even to incorporate it into a sequential block of amino acids, which is then condensed with the deficient part of the peptidic chain.

The present invention is also concerned with a process of preparing a pseudopeptide which is formed by at least one peptidic radical connected by a peptide bond to at least one radical corresponding to one molecule or one derivative of a therapeutically active molecule, characterised in that:

(a) a peptide in acid form, and of which the other functions are protected with a molecule or a derivative of a therapeutically active molecule carrying an amine function and of which the other functions are protected, is condensed in the presence of a condensation agent, or (b) a peptide which is in amine form, and of which the other functions are protected with a molecule or a derivative of a therapeutically active molecule carrying an acid function and of which the other functions are protected, is condensed in the presence of a condensation agent and the protected functions are liberated, if this is necessary.

The synthesis of peptidic chains is known and is carried out by condensation of amino acids, for example, in the presence of DCCD in a solvent such as DMF, methylene chloride or an organic nitrile, or in the presence of an anhydride, such as a chloroformate, for example isobutyl chloroformate, in a solvent such as THF.

In the preparation of pseudopeptides according to the invention, when the active molecule shows a very basic amine function, it may be necessary to effect the condensation in the presence of N-hydroxy-succinimide.

When the reaction is intended for forming a peptide bond, then obviously as is known in the art, the other non-reacting functions of the molecules will be protected, if this should be necessary. The protective groups are also known; for example, for protecting the amine grouping, it is a question of groups of acyl type, such as formyl, phthalyl, etc., or groups of urethane type, such as benzyloxycarbonyl (Cbz) or ter-butyloxycarbonyl (BOC). These groupings can then be eliminated without destroying the peptide bond, for example, under gentle conditions by an acid treatment (hydrochloric acid) or by a treatment with hydrogen bromide in glacial acetic acid or by hydrogenation, particularly for eliminating protective groups such as Cbz, or by treatment with hydrazine, for eliminating the phthalyl grouping.

For example, esters, salts or amides, particularly the methyl or ethyl esters, which are easily able to regenerate the acid function by saponification, are used for protecting the acid groupings.

Should it be necessary, the hydroxyl functions of the compounds can be protected in reaction by esterification or by etherification, particularly with benzyl or tetrahydropyranyl groups. The hydroxyl function can then be regenerated by hydrogenation in the presence of a catalyst.

The abbreviations which are used in the present specification are those which are recommended by IUPAC-IUB, Commission on Biochemical Nomenclature J. Biol. Chem., 241, 2491 (1966) and 242, 555 (1967).

The supplementary abbreviations are:

pGlu = pyroglutamic acid
DCCD = dicyclohexyl carbodiimide
DCCU = dicyclohexyl urea
DMF = dimethylformamide
HONSu = N-hydroxysuccinimide
THF = tetrahydrofuran
Et$_3$N = triethylamine
Cbz = benzyl oxycarbonyl
Bzo = benzyloxy
Amph: amphetamine
PEA: phenylethylamine Amph-Cl: p-chloro-amphetamine
PEA-diBzO: 3,4-dibenzoxyphenyl ethylamine
DA: dopamine
Amph-NO$_2$: p-nitro-amphetamine
Amph-NH$_2$: p-amino-amphetamine
N-Pht-Amph-NH$_2$: N-phthaloyl-4-amino-amphetamine
Try-NH$_2$: tryptamine
PP: 10-(3-aminopropyl)-3-chloro-phenthiazine
BD: 1,3-dihydroxy-5-phenyl-7-amino-1,4-benzodiazepine-2-one
PDD: 5-(3-aminopropylidene)-dibenzo[a,d]cycloheptadi-1,4-ene
PT: 4-ethoxy aniline
AP: 1,5-dimethyl-2-phenyl-4-amino-3-pyrazolone
AB: 4-aminobarbituric acid
NP: 4-phenyl-4-ethoxycarbonyl piperidine The following examples are designed for illustrating the preparation of certain compounds in accordance with the present invention, without however limiting the latter.

The melting points are established with a heating stage microscope.

The infra-red spectra are recorded on a Perkin Elmer IR 457 apparatus, starting from KBr tablets.

The NMR spectra are produced in DMSO-d$_6$ on a JECL C 60HL apparatus (internal reference TMS); the chemical displacements are expressed in ppm.

The thin-film chromatographic results are obtained with GF 254 Merck silica gel sheets, developed in the three following solvents:

1—basic solvent CHCl$_3$—MeOH (4-1) NH$_3$ vapours;
2—acid solvent BuOH—AcOH—AcOEt—water 1-1-1-1;
3—benzene-ethanol 80–20;
3*—benzene-ethanol 50–50.

Detection, ultra-violet 250 μm and iodine.

The results of the microanalysis are indicated by the symbols of the elements, when they are not spaced by more than ±0.4% from the theoretical value.

EXAMPLE 1

Preparation of pGlu-His-OH (a) Methyl ester of pyroglutamyl histidine 9.68 g (0.04 mole) of His-OMe . 2HCl and 4.64 g (0.04 mole) of pGlu are brought into suspension in 160 cc of MeCN, the hydrochloride is decomposed with 11.5 cc (0.08 mole) of Et$_3$N. After addition at 0° C. of 8.16 g (0.04 mole) of DCCD, the mixture is stirred for 24 hours at ambient temperature.

The precipitate which is formed (about 20 g) is filtered, dried and washed with water. The major part of the dicyclohexyl urea which is insoluble in water is hydro-extracted. The aqueous solution is evaporated to dryness, the residue is dried and purified on a column.

Column (diameter 5 cm, height = 80 cm) of 600 g of silica gel 60 Merck.

Elution with 6 liters of the mixture of CH$_2$Cl$_2$ - MeOH (95–5) of the following compounds: DCCU (0.04 mole). Et$_3$N.HCl (traces), His-OMe (traces), and then with 1.5 liters of MeOH of pGlu-His-OMe and then pGlu.

White crystals: 6.5 g; IR (3310, 1750, 1670, 1540, 1275 cm$^{-1}$);

NMR (DMSO): δ=11 (NH$_{im}$His), 8.45 (d, NH His), 7.9 (s, NH pGlu), 7.55 (s, CH 2-His), 6.85 (s. CH 4-His), 4.6 (m, CH-α His), 4.1 (m, CH-α pGlu), 3.6 (s, OCH$_3$), 3.0 (d, CH$_2$ His), 2.1 (m, CH$_2$-β and -γpGlu).

(b) Pyroglutamyl histidine 5.6 g (0.02 mole) of pGlu-His-OMe are dissolved in 200 cc of MeOH and treated while cold for 2 hours with 4.8 g (6×0.02 mole) of NaOH. The solution which is obtained is acidified to pH 4.5 with 6×0.02 mole of HCl. After being evaporated to dryness under vacuum at 50° C., the pGlu-His-OH is obtained, and this can be used without any additional purification. White solid; yield is quantitative.

EXAMPLE 2

Preparation of pGlu-His-Pro-OH (a) Methyl ester of pyroglutamyl histidyl proline To 4.95 g (0.03 mole) of Pro-Me.2 HCl, dissolved in 50 cc of DMF, are added 4.3 cc (0.03 mole) of Et$_3$N. The precipitate of Et$_3$N.HCl is eliminated by filtration. Added to the filtrate are 8 g (0.03 mole) of pGlu-His-OH, prepared by the process of Example 1, in 150 cc of DMF, and then, at 0° C., 6 g (0.03 mole) of DCCD. After stirring for 24 hours at ambient temperature, the precipitate of DCCU is filtered, the DMF is evaporated to dryness and the residue is purified by being passed over a silica gel column, using CH$_2$Cl$_2$-MeOH, 95–5, as eluent.

(b) Pyroglutamyl histidyl proline

The ester as obtained under (a) is saponified under the same conditions as the ester of Example 1(a) then the sodium salt as obtained is acidified to pH 4.5. The pGlu-His-Pro-OH is obtained in the form of colourless crystals.

EXAMPLE 3

Preparation of pGlu-Amph 2.7 g (0.02 mole) of amphetamine and 2.3 g (0.02 mole) of N-hydroxy succinimide are added to 0.02 mole of pyroglutamic acid in DMF; to this solution, cooled to 0° C., is added a solution of 4.12 g (0.02 mole) of DCCD in DMF. After stirring for 24 hours at ambient temperature, the DCCU precipitate is suction-filtered and the filtrate is evaporated to dryness. The pGlu-Amph residue is recrystallised in 95° EtOH.

EXAMPLE 4

Preparation of pGlu-His-Pro-Amph

The operation as disclosed in Example 3 is carried out, but replacing the pyroglutamic acid by pGlu-His-Pro-OH, obtained in Example 2, and the crystallisation is replaced by column chromatography.

Column (diameter 5 cm, height = 40 cm) of 300 g of silica gel, 60 Merck, elution by 4 liters of the CH$_2$Cl$_2$—MeOH (95-5) mixture of the following compounds: DCCD and Et$_3$N.HCl (traces), N-hydroxy succinimide (0.02 mole), and then pGlu-His-Pro-Amph.

NMR (DMSO):δ=11 (NM$_{im}$ His), 8 to 8.4 (NH His, Amph), 7.7 (s, NH pGlu), 7.4 (s, CH 2-His), 7.1 (s. aromatic CH), 6.8 (s, CH 4-His), 4.0 to 4.5 (CH-α His,Glu, Pro), 3.1 to 3.4 (q, CH Amph), 2.4 to 2.8 (CH$_2$ Amph, His, Pro), 2.0 (CH$_2$-β and -γ pGlu), 1.65 (CH$_2$ Pro), 1.15 to 1.25 (d, CH$_3$ Amph).

EXAMPLE 5

Preparation of pGlu-His-Amph

The procedure as indicated in Example 3 is followed, but replacing the pyroglutamic acid by pGlu-His-OH, obtained in Example 1, and the crystallisation is replaced by column chromatography. Column (diameter 5 cm, height=40 cm) of 300 g of silica gel, 60 Merck, elution with 4 liters of the mixture of $CH_2Cl_2$-MeOH(-95-5) of the following compounds: DCCD and $Et_3N.HCl$ (traces), N-hydroxy succinimide (0.02 mole), and then pGlu-His-Amph.

EXAMPLE 6

Preparation of pGlu-His-3,4-dibenzyloxyphenylethyl amine

One mole of pGlu-His-OH, obtained in Example 1, and one mole of 3,4-dibenzyloxyphenylethyl amine are condensed in the cold and in 24 hours in the presence of one mole of N-hydroxy succinimide and one mole of dicyclohexyl carbodiimide in DMF. The dicyclohexy urea being formed is eliminated by filtration, the DMF is evaporate under vacuum at 80° C. and the residue which is obtained is purified by passage through a silica gel column eluted by the solvent consisting of $CH_2Cl_2$-MeOH (95-5), and then MeOH. Recrystallisation takes place in EtOH 95°. The product of the required strength is obtained in the form of white crystals: Mp=238° C., Rf=0.60 ($CHCl_3$-MeOH 4-1+$NH_3$), $[\alpha]_D^{25}$=+10 (c=0.3 MeOH), C, H, N, O for $C_{33} H_{35} N_5 O_5$, yield=43%.

EXAMPLE 7

Preparation of pGlu-His-Dopamine

The benzyl groupings of the compound obtained according to Example 6 are eliminated by catalytic hydrogenation for 4 hours at ambient temperature in the presence of 5% Pd on carbon. The catalyst is filtered and the filtrate is evaporated to dryness. The hydrochloride of pGlu-His-DA is formed by addition of ethyl chloride and recrystallised in MeOH-acetone. White powder, Mp—137° C., Rf=0.64 (BuOH, AcOH—AcOEt—water 1-1-1-1), $[\alpha]_D^{25}$=+20 (c=MeOH), C, H, N, O for $C_{19} H_{23} N_5 O_5 \cdot 2HCl,H_2O$. Yield=35%.

EXAMPLES 8 to 17

By operating in accordance with Example 5, but replacing the amphetamine by:

| | |
|---|---|
| Phenylethylamine, | p-Glu—His—PEA is obtained |
| 4-chloro-Amph, | p-Glu—His—4-Cl—Amph is obtained |
| 4-nitro-Amph, | p-Glu—His—4-nitro-Amph is obtained |
| 4-amino-N—Pht—Amph, | pGlu—His—pNH—Amph—N—Pht is obtained |
| Try—NH2, | pGlu—His—Try—NH2 is obtained |
| PP | pGlu—His—PP is obtained |
| BD | pGlu—His—BD is obtained |
| PDP | pGlu—His—PDD is obtained |
| PT | pGlu—His—PT is obtained |

EXAMPLE 18

The catalytic hydrogenation in the presence of 5% Pd on C, for 2 hours under a pressure of 10 bars and at ambient temperature of the nitro function of the pGlu-His-4-nitro-Amph compound, leads to the compound pGlu-His-4-amino-Amph.

EXAMPLE 19

Preparation of pGlu-His-pNH-Amph 6 g of the peptide pGlu-His-pNH-Amph-N-Pht (0.013 mol) are dissolved in 200 cc of EtOH and 3.25 cc (0.065 mol) of hydrazine in 30 cc of EtOH are added. After heating for 30 minutes under reflux, a phthalhydrazide precipitate is formed and the heating is continued for 30 minutes. After cooling, the phthalhydrazine precipitate is filtered, the filtrate is concentrated, the free peptide which crystallises is recrystallised from EtOH.

EXAMPLE 20

Preparation of Cbz-His-Amph 12.7 g (0.044 mol) of Cbz-His are added to 6 g (0.044 mol) of amphetamine and 5 g (0.044 mol) of N-hydroxysuccinimide in 200 cc of DMF. To the cooled solution are added 9 g (0.044 mol) of DCCD. After 24 hours, the precipitate of DCCU is filtered, the DMF solution is evaporated to dryness and the residue is purified on a silica gel column eluted with the mixture of toluene-10% AcOEt; the peptide obtained by elution can then be recrystallised from EtOH.

EXAMPLE 21

Preparation of His-Amph. 2HBr 4.06 g of Cbz-His-Amph (0.01 mol) are treated for 1 hour in the cold with 15 ml of 15% HBR in AcOH. After evaporating the solvent, the peptide is dissolved in water and the aqueous solution is washed twice with ether. The aqueous solution is then evaporated to dryness and the peptide recrystallised from EtOH-ether.

EXAMPLE 22

Preparation of benzyloxycarbonyl propyl leucine 12.5 g (0.05 mol) of Cbz-Pro are dissolved in 70 cc of THF and 7.5 cc (0.05 mol) of $Et_3N$, and then cooled to $-10°$ C. 6.8 g (0.05 mol) of isobutyl chloroformate in 30 cc of THF are added dropwise, whereafter the mixture is stirred for 20 minutes at $<10°$ C. A solution of 7.9 g (0.06 mol) of Leu and 12.6 cc (0.08 mol) of $Et_3N$ in 65 cc of water are added to the mixture and the reaction is allowed to continue for 90 minutes, allowing the temperature to rise to 20° C. The reaction mixture is acidified with 6N-HCl, the THF is removed under vacuum and the solid which is obtained is dissolved in 20 cc of AcOH and then precipitated with 200 cc of water. Recrystallisation takes place in $CCl_4$. The product indicated in the heading is obtained, this having two melting points: either 118° C. or 136° C.

EXAMPLES 23 to 36

Using the method which is described in Example 3 or in Example 20, it is possible to obtain from

| | |
|---|---|
| Cbz—Pro OH | the compound Cbz—Pro—Amph |
| Cbz—Gly—OH | the compound Cbz—Gly—Amph |

Cbz—Pro—Leu—OH     the compound Cbz—Pro—Leu—Amph

Always using the same method, but employing Cbz-Pro-Leu-OH and different amines, there are obtained from

| | |
|---|---|
| PEA | the compound Cbz—Pro—Leu—PEA |
| Cl—4-Amph | the compound Cbz—Pro—Leu—Cl—4-Amph |
| $NO_2$—4-Amph | the compound Cbz—Pro—Leu—$NO_2$—4-Amph |
| BD | the compound Cbz—Pro—Leu—BD |
| PDD | the compound Cbz—Pro—Leu—PDD |
| PP | the compound Cbz—Pro—Leu—PP |
| PT | the compound Cbz—Pro—Leu—PT |
| AP | the compound Cbz—Pro—Leu—AP |
| NP | the compound Cbz—Pro—Leu—NP |
| Try—$NH_2$ | the compound Cbz—Pro—Leu—Try—$NH_2$ |
| diBzO—PEA | the compound Cbz—Pro—Leu—PEA—diBzO |

EXAMPLES 37 to 51

The benzyloxy grouping of the following compounds is eliminated by dissolving the compound in a 2.5 N solution of hydrogen bromide gas in AcOH at the rate of 0.1 mol per 200 cc. After 1 hour at ambient temperature, the solvent is evaporated and the residue is taken up in water. The aqueous solution, extracted with ether for eliminating the benzyl bromide, is evaporated to dryness and the residue is crystallised from EtOH-ether.

In this manner, the following are obtained, on starting with

| | |
|---|---|
| Cbz—Pro—Amph | the compound Pro—Amph . HBr |
| Cbz—Gly—Amph | the compound Gly—Amph . HBr |
| Cbz—Pro—Leu—Amph | the compound Pro—Leu—Amph . HBr |
| Cbz—Pro—Leu—Gly—Amph | the compound Pro—Leu—Gly—Amph—NHr |
| Cbz—Pro—Leu—Gly—$NH_2$ | the compound Pro—Leu—Gly—$NH_2$ . HBr |
| Cbz—Pro—Leu—Amph—Cl | the compound Pro—Leu—Amph—Cl . HBr |
| Cbz—Pro—Leu—PEA | the compound Pro—Leu—PEA . HBr |
| Cbz—Pro—Leu—Amph—$NO_2$ | the compound Pro—Leu—Amph—$NO_2$ . HBr |
| Cbz—Pro—Leu—BD | the compound Pro—Leu—BD . HBr |
| Cbz—Pro—Leu—PPD | the compound Pro—Leu—PPD . HBr |
| Cbz—Pro—Leu—PP | the compound Pro—Leu—PP . HBr |
| Cbz—Pro—Leu—PT | the compound Pro—Leu—PT . HBr |
| Cbz—Pro—Leu—AP | the compound Pro—Leu—AP . HBr |
| Cbz—Pro—Leu—NP | the compound Pro—Leu—NP . HBr |
| Cbz—Pro—Leu—Try—$NH_2$ | the compound Pro—Leu—Try—$NH_2$ . HBr |

EXAMPLES 52 and 53

The benzyloxy groupings of the following compounds are eliminated by catalytic reduction in the presence of 5% Pd on carbon, under a pressure of 20 bars and over a period of 12 hours at ambient temperature. The catalyst is filtered and the filtrate is evaporated to dryness, whereafter the peptide is recrystallised Cbz-Pro-Leu-PEA-diBzo gives Pro-Leu-DA
Cbz-Pro-Leu-Amph-p$NO_2$ gives Pro-Leu-Amph-$NH_2$.

EXAMPLE 54

Synthesis of NCbz-(Bzo)Tyr-Gly-Gly 4 g (0.01 mol) of NCbz-(BzO)-Tyr and 1.4 cc (0.01 mol) of $Et_3N$ are dissolved in 20 cc of THF and cooled to −10° C. 1.3 cc (0.01 mol) of isobutyl chloroformate are slowly added and stirring takes place for 20 minutes. 1.3 g (0.01 mol) of glycyl glycine and 1.4 cc (0.01 mol) of $Et_3N$ in 10 cc of water are then added, stirring taking place for 1½ hours, while allowing the temperature to rise to ambient temperature. After evaporating the THF, the solution is neutralised with 2 N-HCl, and a precipitate of NCbz(Bzo)-Tyr-Gly-Gly is then formed, this being filtered, washed with water and recrystallised from EtOH.

EXAMPLES 55 and 56

Synthesis of NCbz-(Bzo)-Tyr-Gly-Gly-PT and NCbz-(Bzo)-Tyr-Gly-Gly-AP 1.37 g (0.01 mol) of p-phenetidine or 2.03 g (0.01 mol) of 4-aminoanti=pyrine and 1.15 g (0.01 mol) of N-OH succinimide are dissolved in 10 cc of DMF, 5.19 g (0.01 mol) of NCbz-(Bzo)-Tyr-Gly-Gly in 50 cc of DMF are added, followed by cooling to 0° C. 2.06 g (0.01 mol) of DCCD are added and stirring takes place for 24 hours at ambient temperature. The precipitate of DCCU is filtered and the DMF is evaporated. The residue as obtained is washed in water and with ethyl acetate. The insoluble substance is then recrystallised from alcohol.

EXAMPLES 57 and 58

Synthesis of Tyr-Gly-Gly-PT or Tyr-Gly-Gly-AP

The benzyl and benzyloxy groups are eliminated by catalytic reduction in the presence of 5% Pd on carbon, under a pressure of 20 bars, over a period of 12 hours at ambient temperature.

The catalyst is filtered and the filtrate is evaporated to dryness, whereafter the residue is recrystallised from EtOH, to provide the peptides Tyr-Gly-Gly-PT or Tyr-Gly-Gly-AP

EXAMPLES 59 and 60

By operating as in Example 22, but replacing the Cbz-Pro by Cbz-Pro-Leu.OH and replacing the Leu by Gly-Amph.Hbr, as obtained in Example 38, Cbz-Pro-Leu-Gly-Amph is obtained and this, when processed in the manner according to Examples 37 to 51, yields Pro-Leu-Gly-Amph.

The results of the experiments and the following reaction diagrams set out the main results of the examples.

DIAGRAM 1

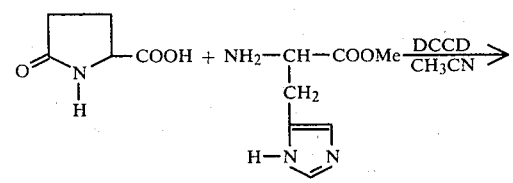

DIAGRAM 1 -continued

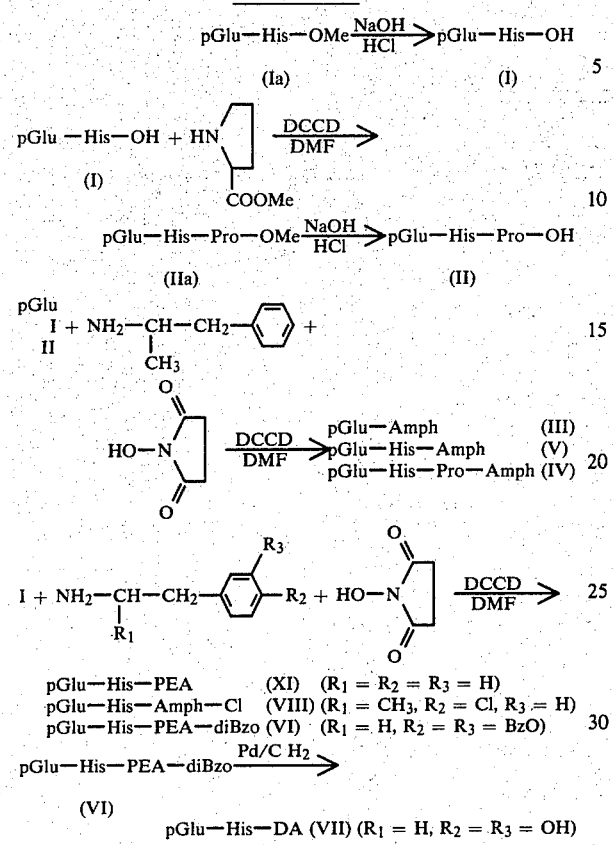

DIAGRAM 2

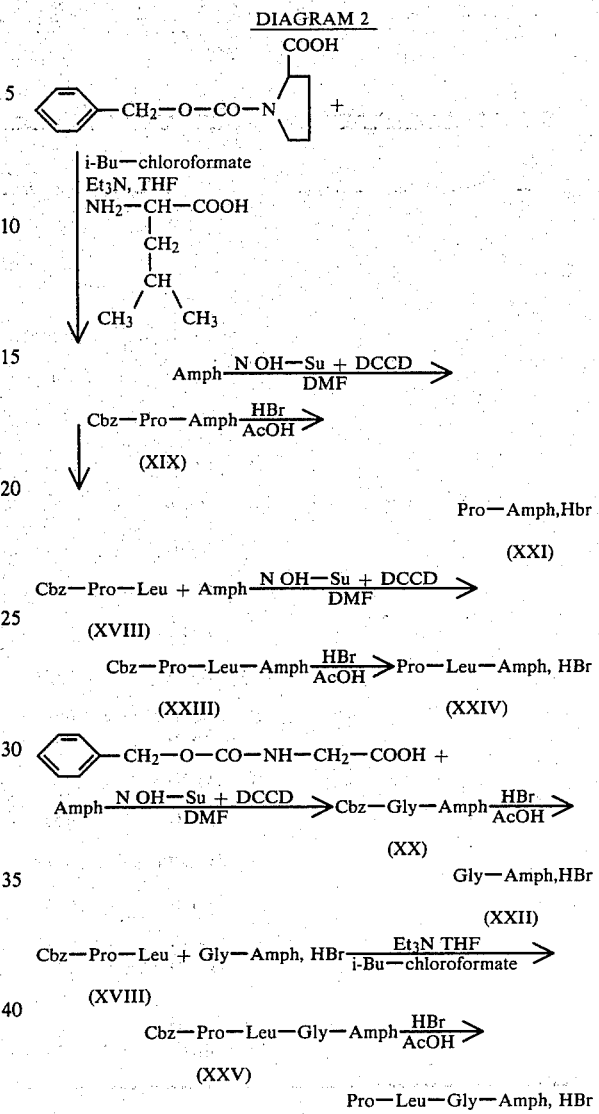

TABLE I

| No. | NAMES | Formula | M.W. | M.P. (°C.) | Yield (%) | Solvent solution |
|---|---|---|---|---|---|---|
| 1 | pGlu—His—OCH$_3$ | C$_{12}$H$_{16}$N$_4$O$_4$ | 280 | 212 | 55 | CH$_2$Cl$_2$ 5% MeOH |
| 2 | pGlu—His—OH | C$_{11}$H$_{14}$N$_4$O$_4$ | 266 | 217 d | — | — |
| 3 | pGlu—His—Pro—OCH$_3$ | C$_{17}$H$_{23}$N$_5$O$_5$ | 377 | 112 | 40 | CH$_2$Cl$_2$ 5% MeOH |
| 4 | pGlu—His—Pro—OH | C$_{16}$H$_{21}$N$_5$O$_5$ | 363 | 150 | — | — |
| 5 | pGlu—Amph | C$_{14}$H$_{18}$N$_2$O$_2$ | 246 | 207 | 64 | — |
| 6 | pGlu—His—Amph | C$_{20}$H$_{25}$N$_5$O$_3$ | 383 | 260 | 44 | CH$_2$Cl$_2$ 20% MeOH |
| 7 | pGlu—His—Pro—Amph | C$_{25}$H$_{32}$N$_6$O$_4$ | 480 | 120 | 49 | CH$_2$Cl$_2$ 20% MeOH |
| 8 | pGlu—His—PEA | C$_{19}$H$_{23}$N$_5$O$_3$ | 369 | 252 | 55 | CH$_2$Cl$_2$ 20% MeOH |
| 9 | pGlu—His—Amph—Cl | C$_{20}$H$_{24}$N$_5$O$_3$Cl | 417.5 | 255 | 53 | CH$_2$Cl$_2$ 20% MeOH |
| 10 | pGlu—His—PEA—diBzO | C$_{33}$H$_{35}$N$_5$O$_5$ | 581 | 238 | 43 | MeOH |
| 11 | pGlu—His—DA | C$_{19}$H$_{23}$N$_5$O$_5$ 2HCl H$_2$O | 492 | 137 | 35 | MeOH |
| 12 | pGlu—His—Amph—NO$_2$ | C$_{20}$H$_{24}$N$_6$O$_5$ | 428 | 290 | 52 | CH$_2$Cl$_2$ 20% MeOH |
| 13 | pGlu—His—Amph—NH$_2$ | C$_{20}$H$_{26}$N$_6$O$_3$ | 398 | 230 | 90 | — |
| 14 | pGlu—His—pNH—Amph—N—Pht | C$_{28}$H$_{28}$N$_6$O$_5$ | 528 | 233 | 41 | CH$_2$Cl$_2$ 20% MeOH |
| 15 | pGlu—His—pNH—Amph | C$_{20}$H$_{26}$N$_6$O$_3$ | 398 | 144 | 44 | CH$_2$Cl$_2$ 50% MeOH |
| 16 | pGlu—His—Try—NH$_2$ | C$_{21}$H$_{24}$N$_6$O$_3$ | 408 | 168 | 52 | — |
| 17 | pGlu—His—PP, HCl | C$_{26}$H$_{27}$N$_6$O$_3$S$_1$,HCl | 575 | 155 | 50 | EtOH |
| 18 | pGlu—His—BD, HCl | C$_{26}$H$_{25}$N$_7$O$_4$, HCl | 535.5 | 212 | 35 | CH$_2$Cl$_2$ 20% MeOH |
| 19 | pGlu—His—PDD, HCl | C$_{29}$H$_{31}$N$_5$O$_3$, HCl | 533.5 | 184 | 50 | — |
| 20 | pGlu—His—PT | C$_{19}$H$_{23}$N$_5$O$_4$ | 385 | 148 | 52 | CH$_2$Cl$_2$ 20% MeOH |

TABLE I-continued

| | | | | | | |
|---|---|---|---|---|---|---|
| 21 | pGlu—His—AP | $C_{22}H_{25}N_7O_4$ | 451 | 123 | 44 | $CH_2Cl_2$ 20% MeOH |
| 22 | pGlu—His—AB | C H N O | | | | |
| 23 | Cbz—His—Amph | $C_{23}H_{26}N_4O_3$ | 406 | 185 | 45 | Tol 10% AcOEt |
| 24 | His—Amph | $C_{15}H_{20}N_4O$ | 272 | 70 | 85 | — |

| No. | Solvent cristallis | Rf 1 | Rf 2 | Micro-analysis | $[\alpha]_D^{22}$ |
|---|---|---|---|---|---|
| 1 | EtOH | 0.34 | 0.53 | CHNO | −0.5° c = 1; MeOH |
| 2 | EtOH | 0 | 0.47 | — | — |
| 3 | — | 0.38 | — | — | −45° c = 1; MeOH |
| 4 | — | 0 | 0.23 | — | — |
| 5 | EtOH | 0.70 | — | CHNO | −3.5° c = 1; MeOH |
| 6 | EtOH | 0.45 | 0.77 | CHNO | +9.5 c = 1; MeOH |
| 7 | — | 0.59 | — | CHNO | −49° c = 1; MeOH |
| 8 | EtOH | 0.43 | — | CHNO | −8° c = 1; MeOH |
| 9 | EtOH | 0.40 | — | CHNOCl | −2.5° c = 1; MeOH |
| 10 | EtOH | 0.60 | — | CHNO | +10° c = 0.3; MeOH |
| 11 | MeOH-acetone | 0 | 0.64 | CHNOCl | +20° c = 1; MeOH |
| 12 | EtOH | 0.44 | — | CHNO | 0° c = 0.24; MeOH |
| 13 | EtOH | 0.64 | — | CHNO | 0° c = 1; MeOH |
| 14 | EtOH AcOEt | 0.50 | — | CHNO | — |
| 15 | EtOH | 0.16 | — | CHNO | +17.5° c = 1; MeOH |
| 16 | EtOH | 0.25 | — | CHNO | −12.5° c = 1; MeOH |
| 17 | EtOH | 0.53 | — | CHNOClS | 0° c = 1; MeOH |
| 18 | EtOH-ether | 0.26 | — | CHNOCl | −10° c = 0.5; MeOH |
| 19 | EtOH | 0.53 | — | CHNOCl | −8° c = 1; MeOH |
| 20 | EtOH-ether | 0.55 | — | | |
| 21 | EtOH-ether | 0.53 | — | | −18° c = 1; MeOH |
| 22 | | | | | |
| 23 | EtOH | 0.5 | — | — | — |
| 24 | EtOH-ether | 0.75 | — | — | −20° c = 1; MeOH |

| No | NAMES | IR cm$^{-1}$ | | | | | NMR δ in ppm |
|---|---|---|---|---|---|---|---|
| 1 | pGlu—His—OCH$_3$ | K Br 1275 | 3310 | 1750 | 1670 | 1540 | DMSO 7.55(s,1H) ; 6.85(s,1H) ; 4.5(m,1H) ; 4.1(m,1H) ; 3.6(s,3H) ; 3.0(d,2H) ; 2.1(m,4H) |
| 2 | pGlu—His—OH | K Br | 3400 | 1670 | 1610 | 1400 | |
| 3 | pGlu—His—Pro—OCH$_3$ | K Br 1630 | 3250 1530 | 2950 1440 | 1730 1260 | 1670 1090 | DMSO 7.5(s,1H) ; 6.8(s,1H) ; 4.2(m,3H) ; 3.6(s,3H) ; 3.5(m,2H) ; 2.8(m,2H) ; 2.0(m,8H) |
| 4 | pGlu—His—Pro—OH | 3400 | 3250 | 1680 | 1610 | 1450 | |
| 5 | pGlu—Amph | 3250 1260 | 1680 1140 | 1660 750 | 1560 700 | 1445 500 485 370 | DMSO 7.2(s,5H) ; 4.0(m,2H) ; 2.7(d,2H) ; 2.0 (m,4H) ; 1.2(d,3H) |
| 6 | pGlu—His—Amph | 3280 700 | 1665 620 | 1645 | 1530 | 1270 | DMSO 7.9(s,1H) ; 7.2(s,5H) ; 6.8(s,1H) ; 4.3 (m,1H) ; 4.0(m,1H) ; 3.4(m,1H) ; 2.7(m,4H) ; 2.0(m,4H) ; 1.0(d,3H) |
| 7 | pGlu—His—Pro—Amph | 3250 | 2970 | 2920 | 2780 | 1700 | DMSO 7.4(s,1H) ; 7.1(s,5H) ; 6.8(s,1H) ; 4.5 (m,1H) ; 4.1(m,3H) ; 3.2(m,2H) ; 2.8(m,2H) ; 2.4(m,2H) ; 2.0(m,4H) ; 1.65(m,4H) ; 1.2(d,3H) |
| 8 | pGlu—His—PEA | 3300 1540 | 3270 1275 | 1670 700 | 1650 620 | 1560 | DMSO 7.4(s,1H) ; 7.1(s,5H) ; 6.8(s,1H) ; 4.4 (m,1H) ; 4.0(m,1H) ; 3.2(m,2H) ; 2.7(m,4H) ; 2.1(m,4H) |
| 9 | pGlu—His—Amph—Cl | 3280 1490 800 | 1685 1270 620 | 1640 1090 | 1540 1015 | 1530 985 | DMSO 7.5(s,1H) ; 7.2(s,4H) ; 6.7(s,1H) ; 4.5 (m,1H) ; 4.0(m,1H) ; 3.9(m,1H) ; 2.8(m,2H) ; 2.5(m,2H) ; 2.1(m,4H) ; 1.0(d,4H) |
| 10 | pGlu—His—PEA—diBzO | 3290 1140 | 1665 1010 | 1645 700 | 1535 630 | 1275 | AcOD 8.7(s,1H) ; 7.4(s,13H) ; 7.0(s,1H) ; 5.1 (s,2H) ; 4.2(m,2H) ; 3.3(m,2H) ; 2.7(m,4H) ; 2.4(m,4H) |
| 11 | pGlu—His—DA | 3380 1440 | 3250 1250 | 1670 1120 | 1640 | 1520 | DMSO 7.4(m,4H) ; 6.9(s,1H) ; 4.4(m,1H) ; 4.0(m,1H) ; 3.2(m,2H) ; 2.7(m,4H) ; 2.1(m,4H) |
| 12 | pGlu—His—Amph—NO$_2$ | 3280 1525 | 3190 1510 | 2910 1340 | 1665 1265 | 1650 740 620 | DMSO 7.7(q,4H) ; 7.4(s,1H) ; 6.7(s,1H) ; 4.4 (m,1H) ; 4.0(m,1H) ; 3.8(m,1H) ; 2.8(m,2H) ; |

-continued

| No | NAMES | IR cm⁻¹ | | | | | NMR δ in ppm |
|----|-------|---------|---|---|---|---|---|
| 13 | pGlu—His—Amph—NH$_2$ | 3380 | 3270 | 3050 | 2950 | 2910 | 2.0(m,4H) ; 1.1(d,3H) |
|  |  | 1665 | 1630 | 1610 | 1530 | 1505 | DMSO 7.4(s,1H) ; 6.5(q,4H) ; 6.7(s,1H) ; 4.4 |
|  |  | 1260 | 1240 | 1120 | 1075 | 975 | (m,1H) ; 4.2(m,1H) ; 4.0(m,1H) ; 2.5(m,2H) ; |
|  |  | 690 | 610 |  |  |  | 2.0(m,4H) ; 1.8(m,2H) ; 1.0(d,3H) |
| 14 | pGlu—His—pNH—Amph—N—Pht | 3400 | 3280 | 1760 | 1690 | 1650 | DMSO 7.7(s,5H) ; 7.5(s,1H) ; 7.1(q,4H) ; |
|  |  | 1520 | 1385 | 1370 | 1260 | 760 | 6.7(s,1H) ; 4.5(m,2H) ; 4.0(m,1H) ; 2.9 (m,2H) ; 2.4(m,2H) ; 2.0(m,4H) ; 1.4(d,3H) |
| 15 | pGlu—His—pNH—Amph | 3260 | 1650 | 1580 | 1510 | 1260 | DMSO 7.3(s,1H) ; 7.1(q,4H) ; 6.7(s,1H) ; 4.4 |
|  |  | 1070 | 970 | 800 | 670 | 610 | (m,1H) ; 4.3(m,1H) ; 4.0(m,1H) ; 2.8(m,2H) ; 2.4(m,2H) ; 2.0(m,4H) ; 0.9(d,3H) |
| 16 | pGlu—His—Try—NH$_2$ | 3320 | 3240 | 3160 | 3095 | 2880 | DMSO 7.5(s,1H) ; 7.0(m,4H) ; 6.8(s,1H) ; 4.5 |
|  |  | 1660 | 1545 | 1460 | 1430 | 1300 | (m,1H) ; 4.1(m,1H) ; 3.3(m,4H) ; 2.8(m,2H) ; |
|  |  | 1270 | 1095 | 740 | 620 |  | 2.0(m,4H) |
| 17 | pGlu—His—PP, HCl | 3260 | 1660 | 1570 | 1560 | 1470 | DMSO 8.95(s,1H) ; 7.2(s,1H) ; 7.0(m,7H) ; 4.5 |
|  |  | 1250 | 750 | 630 |  |  | (m,2H) ; 3.9(m,2H) ; 3.1(m,4H) ; 2.0(m,6H) |
| 18 | pGlu—His—BD, HCl | 3250 | 2940 | 1670 | 1550 | 1500 | DMSO 8.8(s,1H) ; 7.2(s,1H) ; 7.4(m,8H) ; 4.5 |
|  |  | 1240 | 1090 | 1035 | 1020 | 890 | (m,2H) ; 4.0(m,2H) ; 2.9(m,2H) ; 2.0(m,4H) |
|  |  | 835 | 790 | 750 | 700 |  |  |
| 19 | pGlu—His—PDD, HCl | 3400 | 3260 | 3100 | 2940 | 1660 | DMSO 8.8(s,1H) ; 7.1(s,1H) ; 7.0(m,8H) ; 4.7 |
|  |  | 1550 | 1490 | 1450 | 1270 | 1255 | (m,1H) ; 4.4(m,1H) ; 4.0(m,1H) ; 3.0(m,6H) ; |
|  |  | 785 | 630 |  |  |  | 2.0(m,4H) |
| 20 | pGlu—His—PT | 3200 | 1660 | 1630 | 1500 | 1230 | DMSO 8.4(s,1H) ; 7.1(s,1H) ; 7.0(q,4H) ; |
|  |  | 1170 | 1110 | 1040 | 820 | 620 | 4.6(m,1H) ; 4.0(m,1H) ; 3.9(q,2H) ; 3.0 (m,2H) ; 2.0(m,4H) ; 1.2(t,3H) |
| 21 | pGlu—His—AP | 3400 | 3240 | 2920 | 1660 | 1490 | DMSO 11.7(s,1H) ; 8.2(s,1H) ; 8.1(s,1H) ; |
|  |  | 1450 | 1430 | 1310 | 1250 | 1140 | 7.9(s,1H) ; 7.7(s,1H) ; 7.3(m,4H) ; 6.9 |
|  |  | 1100 | 770 | 700 |  |  | (s,1H) ; 4.6(m,1H) ; 4(m,1H) ; 3(m,5H) ; 2.0(m,7H) |
| 22 | pGlu—His—AB |  |  |  |  |  |  |
| 23 | Cbz—His—Amph | 3340 | 3240 | 3160 | 2980 | 2650 | DMSO 7.45(s,1H) ; 7.2(s,5H) ; 7.1(s,5H) ; 6.7 |
|  |  | 1690 | 1540 | 1520 | 1265 | 1110 | (s,1H) ; 5.0(s,2H) ; 4.2(m,1H) ; 4.0(m,1H) ; |
|  |  | 1030 | 950 | 875 | 760 | 700 | 2.8(m,4H) ; 1.0(d,3H) |
| 24 | His—Amph | 3400 | 1640 | 1520 | 1430 | 1370 |  |
|  |  | 1220 | 1140 | 1080 | 820 | 740 |  |
|  |  | 700 | 670 |  |  |  |  |

TABLE II

| No | NAMES | Formula | M.W. | M.P. (°C.) | Yield (%) |
|----|-------|---------|------|-----------|-----------|
| 25 | Cbz—Pro | C$_{13}$H$_{15}$NO$_4$ | 249 | 75 | 82 |
| 26 | Cbz—Pro—Leu | C$_{19}$H$_{26}$N$_2$O$_5$ | 362 | 118 | 77 |
| 27 | Cbz—Pro—Amph | C$_{22}$H$_{26}$N$_2$O$_3$ | 366 | 92 | 74 |
| 28 | Cbz—Pro—Leu—Amph | C$_{28}$H$_{37}$N$_3$O$_4$ | 479 | 135 | 43 |
| 29 | Cbz—Gly | C$_{10}$H$_{11}$N$_1$O$_4$ | 209 | 120 | 72 |
| 30 | Cbz—Gly—Amph | C$_{19}$H$_{22}$N$_2$O$_3$ | 326 | 90 | 54 |
| 31 | Gly—Amph, HBr | C$_{11}$H$_{17}$N$_2$OBr | 273 | 186 | 80 |
| 32 | Cbz—Pro—Leu—Gly—Amph | C$_{30}$H$_{40}$N$_4$O$_5$ | 536 | 149 | 48 |
| 33 | Cbz—Pro—Leu—Gly—NH$_2$ | C$_{21}$H$_{30}$N$_4$O$_5$ | 418 | 164 | — |
| 34 | Cbz—Pro—Leu—Amph—Cl | C$_{28}$H$_{36}$ClN$_3$O$_4$ | 513.5 | 115 | 83 |
| 35 | Cbz—Pro—Leu—PEA | C$_{27}$H$_{35}$N$_3$O$_4$ | 465 | 117 | 78 |
| 36 | Cbz—Pro—Leu—Amph—NO$_2$ | C$_{28}$H$_{36}$N$_4$O$_6$ | 500.62 | 150 | 72 |
| 37 | Cbz—Pro—Leu—BD | C$_{34}$H$_{36}$N$_5$O$_5$ | 594.62 | 220 | 60.9 |
| 38 | Cbz—Pro—Leu—PDD | C$_{37}$H$_{43}$N$_3$O$_4$ | 593 | 180 | 80 |
| 39 | Cbz—Pro—Leu—PP | C$_{34}$H$_{39}$N$_4$O$_4$S | 634 | 65 | 42 |
| 40 | Cbz—Pro—Leu—PT | C$_{27}$H$_{35}$N$_3$O$_5$ | 481 | 156 | 62 |
| 41 | Cbz—Pro—Leu—AP | C$_{30}$H$_{37}$N$_5$O$_5$ | 547 | oil | 44 |
| 42 | Cbz—Pro—Leu—NP | C$_{33}$H$_{43}$N$_3$O$_6$ | 577 | oil | 76 |
| 43 | Cbz—Pro—Leu—Try—NH$_2$ | C$_{29}$H$_{36}$N$_4$O$_4$ | 504 | 199 | 87 |
| 44 | Cbz—Pro—Leu—PEA—diBzO | C$_{41}$H$_{47}$N$_3$O$_6$ | 677 | 158 | 98 |

| No | Solvent cristal. | Rf1 | Rf3 | micro-analysis | $[\alpha]_D^{22}$ |
|----|------------------|-----|-----|----------------|---------|
| 25 | CCl$_4$ | 0.2 | 0.3 | — | −61.5° c = 5; CH$_3$COOH |
| 26 | CCl$_4$ | 0.2 | 0.3 | — | −63±1 C = 5; MeOH |
| 27 | Cyclohexane | — | 0.7 | CHNO | −51.5±0.05 C = 2; MeOH |
| 28 | Cyclohexane | 0.9 | 0.5 | CHNO | −65±3 C = 0.43; MeOH |
| 29 | ether | — | — | — | — |
| 30 | EtOH | 1 | 0,5 | CHNO | −2±1 C = 1; MeOH |
| 31 | EtOH—ether | 0.73 | — | CHNOBr | 0 |
| 32 | Cyclohexane—AcOEt | — | 0.44 | CHNO | −30.5±1 C = 1; MeOH |
| 33 | AcOEt | 0.65 | — | — | −73° |

TABLE II-continued

|    |                    |      |      |      |              |
|----|--------------------|------|------|------|--------------|
| 34 | Hexane—Acetone     | 1.0  | 0.52 | —    | C = 2; EtOH  |
| 35 | Cyclohexane—AcOEt  | 1.0  | 0.83 |      |              |
| 36 | Cyclohexane—CCl₄   |      | 0.68 |      |              |
| 37 | —                  |      | 0.89 |      |              |
| 38 | EtOH               | 1.0  | 0.55 | —    | −58° C = 0.5; MeOH |
| 39 | Cyclohexane        | 0.95 | 0.8  | —    | −50° C = 0.7; MeOH |
| 40 | Cyclohexane—CCl 4  | 0.76 | —    | —    |              |
| 41 |                    | 0.74 |      |      |              |
| 42 |                    | 0.95 |      |      |              |
| 43 | EtOH               | 0.98 | 0.33 |      |              |
| 44 | EtOH               | 1    | 0.6  |      |              |

| No | NAMES | I R cm$^{-1}$ | N M R δ in ppm |
|----|-------|---------------|----------------|
| 25 | Cbz—Pro | 3000 1750 1640 1440 1360 1330 1320 1210 1190 1120 1080 750 700 | CDCl₃ 7.1(s,5H); 5.0(s,2H); 4.2(m,1H); 3.3 (m,2H); 2.0(m,4H) |
| 26 | Cbz—Pro—Leu | 3340 2980 1740 1660 1540 1450 1370 1200 1150 770 730 700 | CDCl₃ 7.2(s,5H); 5.1(s,2H); 4.3(m,2H); 3.5 (m,2H); 2.0(m,4H); 1.6(m,3H); 0.9(m,6H) |
| 27 | Cbz—Pro—Amph | 3310 2980 2930 1700 1660 1540 1420 1360 1240 1180 1130 770 730 700 690 | CDCl₃ 7.3(s,5H); 7.2(s,5H); 5.1(s,2H); 4.3 (m,2H); 3.5(m,2H); 2.7(d,2H); 2.0(m,4H); 1.1(d,3H) |
| 28 | Cbz—Pro—Leu—Amph | 3300 3100 2980 1715 1650 1560 1430 1365 1290 1245 1185 1130 780 750 740 710 | DMSO 7.3(s,5H); 7.1(s,5H); 5.0(d,2H); 4.2 (m,3H); 3.3(m,2H); 2.7(d,2H); 1.8(m,4H); 1.4(m,3H); 1.1(d,3H); 0.9(d,6H) |
| 29 | Cbz—Gly | — | |
| 31 | Cbz—Gly—Amph | 3330 3040 3020 2960 2920 1690 1650 1525 1445 1370 1280 1240 1160 1050 725 690 | DMSO 7.3(s,5H); 7.1(s,5H); 5.0(s,2H); 4.0 (q,1H); 3.6(d,2H); 2.7(m,2H); 1.1(d,3H) |
| 32 | Cbz—Pro—Leu—Gly—Amph | 3280 3050 2940 2910 2860 1700 1630 1535 1410 1345 1220 1115 760 740 730 690 | DMSO 7.2(s,5H); 7.1(s,5H); 5.0(d,2H); 4.2 (m,2H); 4.0(m,1H); 3.5(m,2H); 3.4(m,2H); 2.7(m,2H); 1.9(m,4H); 1.5(m,3H); 1.0(d,3H) 0.9(d,6H) |
| 33 | Cbz—Pro—Leu—Gly—NH₂ | 3420 3360 3320 2960 2880 1740 1670 1510 1470 1435 1365 1330 1215 1130 1000 775 735 700 | DMSO 7.3(s,5H); 5.0(d,2H); 4.3(m,2H); 3.5 (m,2H); 3.4(m,2H); 1.9(m,4H); 1.5(m,3H); 0.8(d,6H) |
| 34 | Cbz—Pro—Leu—Amph—Cl | 3305 3070 1725 1695 1655 1535 | CDCl₃ 7.25(s,5H); 7.10(s,4H); 5.05(s,2H); 4.25(m,2H); 3.5(m,2H); 3(m,2H); 2(m,4H); 1.5(m,3H); 1.25(d,3H); 0.85(d,6H) |
| 35 | Cbz—Pro—Leu—PEA | 3300 3070 1725 1705 1645 1545 | CDCl₃ 7.25(s,5H); 7.15(s,5H); 6.95(m,1H); 6.85 (m,1H); 5.1(s,2H); 4.35(m,2H); 3.55(m,4H); 2.8(m,2H); 2(m,4H); 1.6(m); 0.90(d,6H) |
| 36 | Cbz—Pro—Leu—Amph—NO₂ | 3300 3035 1765 1720 1600 1530 1350 860 805 | CDCl₃ 8.73(q,4H); 7.2(s,5H); 6.45(s,1H); 6.35 (s,1H); 5.1(d,2H); 4.2(m,3H); 3.45(m,2H); 2.8(d,2H); 2(m,4H); 1.45(m,2H); 1.1(d,3H); 0.85(d,6H) |
| 37 | Cbz—Pro—Leu—BD | 3310 2950 1710 1660 770 700 | |
| 38 | Cbz—Pro—Leu—PDD | 3300 3030 2930 1715 1690 1640 1530 1420 1350 1110 770 760 740 705 | CDCl₃ 7.3(s,5H); 7.1(s,8H); 5.8(m,1H); 5.0 (s,2H); 4.2(m,2H); 3.4(s,2H); 3.2(m,4H); 2.0(m,4H); 1.6(m,3H); 0.9(d,6H) |
| 39 | Cbz—Pro—Leu—PP | 3280 3060 2920 2860 1710 1690 1640 1550 1440 1410 1350 1240 1110 750 695 | |
| 40 | Cbz—Pro—Leu—PT | 3290 1720 1690 1645 1510 1250 1045 825 | CDCl₃ 7.23(s,5H); 6.73(d,2H); 5.09(s,2H); 3.96(q,2H); 3.5(m,2H); 2.02(m,4H); 1.38(t,3H) 0.94(q,3H); 0.88(s,3H) |
| 41 | Cbz—Pro—Leu—AP | | CDCl₃ 7.20(s,10H); 5.05(s,2H); 4.30(m,1H); 3.47(m,2H); 2.72(s,3H); 2.0(m,2H); 1.75(m,2H) 1.43(s,3H); 0.92(m,6H) |
| 42 | Cbz—Pro—Leu—NP | 3300 1690 1650 1520 1240 1040 820 740 | |
| 43 | Cbz—Pro—Leu—Try—NH₂ | 3300 1685 1645 1530 | CDCl₃ 7.20(m,10H); 5.05(s,2H); 4.25(m,2H) 3.45(m,2H); 2(m,4H); 1.35(m,3H); 0.85(d,6H) |
| 44 | Cbz—Pro—Leu—PEA—diBzO | 3295 3070 1690 1640 1535 1515 | CDCl₃ 7.20(m,15H); 6.70(m,3H); 5.05(s,6H) 4.20(m,2H); 3.35(m,4H); 2.7(m,2H); 1.95 (m,4H); 1.55(m,3H); 0.85(d,6H) |

TABLE III

| No | NAMES | Formula | M.W. | M.P. (°C.) | Yield |
|----|-------|---------|------|------------|-------|
| 46 | Pro—Amph, HBr | C₁₄H₂₁N₂O₁Br | 313 | 190 | 76 |
| 47 | Pro—Leu—Amph, HBr | C₂₀H₃₂N₃O₂Br | 426 | 115 | 35 |
| 48 | Pro—Leu—Gly—Amph, HBr | C₂₂H₃₅N₄O₃Br | 483 | 110 | 90 |
| 49 | Pro—Leu—Gly—NH₂, HBr | C₁₃H₂₅N₄O₃Br | 365 | 195 | 75 |
| 50 | Pro—Leu—Amph—Cl, HBr | C₂₀H₃₁ClN₃O₂ | 460.5 |  | 75 |

TABLE III-continued

| No. | Names | Formula | MW | mp | Yield |
|---|---|---|---|---|---|
| 51 | Pro—Leu—PEA, HBr | $C_{19}H_{30}BrN_3O_2$ | 412 | — | 83 |
| 52 | Pro—Leu—Amph—NO$_2$, HBr | $C_{20}H_{31}BrN_4O_4$ | 471.06 | 125 | 95 |
| 53 | Pro—Leu—Amph—NH$_2$ | $C_{20}H_{32}N_4O_2$ | 360.45 | 92 | 71 |
| 54 | Pro—Leu—BD, HBr | $C_{26}H_{31}BrN_5O_3$ | 541.45 | 220 | 88.1 |
| 55 | Pro—Leu—PPD | $C_{29}H_{37}N_3O_2$, HBr | 540 | 130 | 76 |
| 56 | Pro—Leu—PP, HBr | $C_{26}H_{33}N_4O_2S_1Cl_1$, HBr | 581.5 | 95 | 80 |
| 57 | Pro—Leu—PT, HBr | $C_{19}H_{30}N_3O_3Br$ | 428 | 129 | 53 |
| 58 | Pro—Leu—AP, HBr | $C_{22}H_{32}N_5O_3Br$ | 494 |  | 80 |
| 59 | Pro—Leu—MP | | | | |
| 60 | Pro—Leu—Try—NH$_2$ | | | | |
| 61 | Pro—Leu—DA | $C_{19}H_{29}N_3O_4$ | 363 | 107 | 70 |
| 62 | Pro—Leu—AP | | | | |

| No. | Solvent cristal | Rf1 | Rf3 | Micro-analysis | $[\alpha]_D^{22}$ |
|---|---|---|---|---|---|
| 46 | EtOH-ether | 0.82 | — | CHNOBr | $-27.5 \pm 1$ c = 1, MeOH |
| 47 | EtOH-ether | 1.0 | *0.70 | CHNOBr | $-30 \pm 4$ c = 1, MeOH |
| 48 | EtOH-ether | 0.81 | *0.62 | CHNOBr | $-23 \pm 1$ c = 1, NaOH |
| 49 | EtOH-ether | 1.0 | *0.45 | — | — |
| 50 | — | 0.93 | 0.08 | | |
| 51 | — | 0.9 | 0.1 | | |
| 52 | — | 0.75 | | | |
| 53 | EtOH-ether | 0.80 | | | |
| 54 | — | 0.52 | | | |
| 55 | EtOH-ether | 0.95 | *0.50 | | $-33°$ c = 1, NaOH |
| 56 | EtOH-ether | 0.95 | *0.50 | | $-27°$ c = 1, NaOH |
| 57 | EtOH-ether | — | 0.09 | CHNOBr | |
| 58 | | — | 0.1 | | |
| 59 | | | | | |
| 60 | | | | | |
| 61 | EtOH | 0.50 | 0.05 | | |
| 62 | | | | | |

| No | NAMES | IR cm$^{-1}$ | NMR δ in ppm |
|---|---|---|---|
| 46 | Pro—Amph, HBr | 3200 3060 2820 2680 2530 2400 1655 1560 1440 1380 1290 1280 1020 990 695 | DMSO 7.2(s,5H); 4.1(m,2H); 3.2(m,2H); 2.7 (d,2H); 1.6(m,4H); 1.0(d,3H) |
| 47 | Pro—Leu—Amph, HBr | 3400 3200 3040 2940 2850 2720 1660 1645 1540 1450 1380 1250 1150 735 690 | DMSO 7.1(s,5H); 4.1(m,3H); 3.1(m,2H); 2.7 (d,2H); 1.8(m,4H); 1.2(m,3H); 1.1(d,3H); 0.8(d,6H) |
| 48 | Pro—Leu—Gly—Amph, HBR | 3200 3040 2940 2860 2720 1650 1540 1450 1375 1240 1150 1080 1020 935 740 690 | DMSO 7.1(s,5H); 4.2(m,2H); 3.9(m,1H); 3.5 (m,2H); 3.2(m,2H); 2.6(m,2H); 1.8(m,4H); 1.5(m,3H); 1.0(d,3H); 0.9(d,6H) |
| 50 | Pro—Leu—Amph—Cl,HBr | 1645 1530 1440 1085 1010 825 | |
| 51 | Pro—Leu—PEA, HBr | 1650 1545 1455 750 700 | |
| 52 | Pro—Leu—Amph—NO$_2$ HBR | 3220 1650 1515 1350 860 800 | DMSO 8.4(s,1H); 8.3(s,1H); 7.9, 7.4(q,4H); 8(s,1H); 4.5(s,1H); 4.2(m,2H); 3.15(m,2H); 2.8(d,2H); 1.8(m,4H); 1.4(m,3H); 1.1(d,3H); 0.8(d,6H) |
| 53 | Pro—Leu—Amph—NH$_2$ | 3270 2930 1650 1250 860 815 | DMSO 8.6(s,1H); 7.6(m,1H); 6.65(q,4H); 5.4 (s,2H); 4.2(m,2H); 4(m,1H); 3.15(s,2H); 2.5(m,2H); 1.85(m,4H); 1.5(m,3H); 1.1(d,3H); 0.9(d,6H) |
| 54 | Pro—Leu—BD, HBr | 3200 1700 1620 1480 840 770 720 | DMSO 10(s,1H); 9.2(m,2H); 7.6(s,5H); 7.2 (m,3H); 6.1(s,1H); 4.3(m,4H); 3.2(m,2H); 1.9(m,4H); 1.65(m,3H); 0.9(d,6H) |
| 55 | Pro—Leu—PDD, HBr | 3400 3300 3060 2920 1650 1540 1440 1360 1250 750 | DMSO 8.54(m,2H); 8.12(m,1H); 5.75(m,1H); 7.1(m,8H); 4.20(m,2H); 3.1(m,6H); 2.22 (m,2H); 1.8(m,2H); 1.55(m,2H); 0.92(s,3H); 0.82(s,3H) |
| 56 | Pro—Leu—PP, HBr | 3400 3240 3050 2950 1650 1550 1450 1240 750 | DMSO 9.55(m,1H); 8.7(m,1H); 8.2(m,1H); 7.10(s,7H); 4.3(m,3H); 4(m,1H); 3.25(m,4H); 2(m,6H); 1.55(m,3H); 0.9(d,6H) |
| 57 | Pro—Leu—PT, HBr | 3420 3230 1655 1540 1510 1240 1045 830 | DMSO 9.45(m,1H); 8.82(m,2H); 7.45(d,2H); 6.80 (d,2H); 3.95(q,2H); 3.20(m,2H); 1.87(m,2H); 1.61(m,3H); 1.32(t,3H); 0.98(s,3H); 0.90(s,3H) |
| 58 | Pro—Leu—AP | | |
| 59 | Pro—Leu—NP | | |
| 60 | Pro—Leu—Try—NH$_2$ | | |
| 61 | Pro—Leu—DA | 1655 1545 1440 1360 1280 1250 1110 | DMSO + CDCl$_3$ 6.3(m,6H); 4.10(m,1H); 3.20 (m,4H); 1.7(m,7H); 0.9(d,6H) |

| No | NAMES | I R cm⁻¹ | N M R δ in ppm |
|---|---|---|---|
| 62 | Pro—Leu—AB | | |

TABLE IV

| No | NAMES | Formula | M.W. | F°C. | Yield | Solvent cristal. | Rf1 | Rf3 | micro-analysis | $[\alpha]_D^{22}$ |
|---|---|---|---|---|---|---|---|---|---|---|
| 63 | N—Cbz—(OBz)—Tyr | $C_{24}H_{23}N_1O_5$ | 405 | 115 | 84 | AcOEt—hex | 0.3 | — | — | 11.5 c = 0.5 AcOH |
| 64 | N—Cbz—(OBz)—Try—Gly—Gly | $C_{28}H_{29}N_3O_7$ | 519 | 133 | 75 | AcOEt—hex | 0.1 | — | — | |
| 65 | N—Cbz—(OBz)—Tyr—Gly—Gly—PT | $C_{36}H_{38}N_4O_7$ | 638 | 188 | 80 | EtOH | 0.7 | | | |
| 66 | NCbz—(Obz)—Try—Gly—Gly—AP | $C_{39}H_{40}N_6O_7$ | 704 | 255 | 80 | EtOH | 0.85 | | | |
| 67 | Try—Gly—Gly—PT | $C_{21}H_{26}N_4O_5$ | 414 | | | | | | | |
| 68 | Try—Gly—Gly—AP | $C_{24}H_{28}N_6O_5$ | 480 | | | | | | | |

| No | NAMES | I R cm⁻¹ | | | | | | N M R δ in ppm |
|---|---|---|---|---|---|---|---|---|
| 63 | NCbz—(OBz)—Tyr | 3300 1500 1050 | 3140 1440 720 | 3020 1380 690 | 1720 1310 | 1680 1230 | 1520 1170 | CDCl 9.4(s,1H) ; 7.2(s,5H) ; 7.1(s,5H) ; 6.8 (q,4H) ; 5.0(s,2H) ; 4.9(s,2H) ; 4.5(s,1H) ; 3.0(d,2H) |
| 64 | NCbz—(OBz)—Tyr—Gly | 3280 1500 | 3140 1230 | 3080 1020 | 2910 720 | 1690 685 | 1640 | DMSO 7.2(s,5H) ; 7.1(s,5H) ; 6.8(q,4H) ; 5.0 (s,2H) ; 4.9(s,2H) ; 4.2(m,1H) ; 3.7(m,4H) ; 2.9(m,2H) |
| 65 | NCbz—(OBz)—Tyr—Gly—Gly—PT | 3300 815 | 1690 735 | 1650 | 1510 | 1235 | 1045 | DMSO 9.7(s,1H) ; 8.12(m,2H) ; 7.25(m,15H) ; 6.80(m,4H), 5(s,2H), 4.9(s,2H), 4.2(m,1H) ; 3.8(m,6H), 2.83(m,2H), 1.28(t,3H) |
| 66 | NCbz—(OBz)—Tyr—Gly—Gly—AP | 3260 1410 | 3060 1310 | 2920 1260 | 1690 1220 | 1660 1030 | 1630 700 | DMSO 9(s,1H) ; 8.1(m,3H) ; 7.2(m,15H) ; 6.8(m,4H) ; 5(d,2H) ; 4.2(m,1H) ; 3.8(m,4H) 2.8(m,2H) ; 3(s,3H) ; 2.1(s,3h). |
| 67 | Tyr—Gly—Gly—PT | | | | | | | |
| 68 | Tyr—Gly—Gly—AP | | | | | | | |

Hereinafter investigated are the pharmacological properties of certain pseudopeptides which contain amphetamine and dopamine as active molecule.

(I) Amphetamic pseudopeptides

For illustrating the interesting features of the pseudopeptides, only three tests have been used for the preliminary study, which tests show the advantage of being easily adaptable to a kinetic investigation:
   action on the rectal temperature in the mouse.
   induction of stereotypes in the rat,
   study of the toxicity in the mouse.

A comparison of these three substances, pGlu-Amph, pGlu-His-Amph and pGlu-His-Pro-Amph, with amphetamine, has been able to be carried out as follows; for this purpose, the products were administered systematically by intraperitoneal route and by oral route, it being possible for this latter procedure to verify the generally admitted assertion of a gastric hydrolysis of peptides; in this case, the action of the amphetamine should be integrally re-established.

A—Action on the rectal temperature in respect of the mouse (1) Intraperitoneal route In a small does (1 mg/kg) the amphetamine causes a hypothermia, 30 minutes after its injection. From 4 mg/kg, a hyperthermia appears immediately 30 minutes after the administration. The temperature of the treatments is once again connected with that of the controls after 2 hours.

The action of pGlu-Amph is very close to that of amphetamine. The smallest dose (5 mg/kg) also causes a hypothermia. From 10 mg/kg. there is immediately found a hyperthermia, of which the maximum is slightly offset in time with respect to amphetamine (1 hour instead of 30 minutes). The period of the action is the same. There is substantially found the effect of the dose of amphetamine contained in pGlu-Amph.

pGlu-His-Amph, whatever may be the injected dose, always produces a hypothermia 30 minutes after its administration. A hyperthermia proportional to the administered dose appears above 50 mg/kg; its maximum is at approximately 3 hours after the injection.

The action of pGlu-His-Pro-Amph approaches very close to that of amphetamine: hypothermia 30 minutes after injection in small doses (12.5 and 25 mg/kg), and hyperthermia immediately from 50 mg/kg. After 5 hours, the temperature of the treated animals nevertheless remains higher than that of the control animals.

(2) Oral route

The action of the amphetamine is substantially the same as when applied intraperitoneally. Only a slight shift in the doses is observed: 4 mg/kg still cause a hypothermia by the oral route, while hyperthermia already appears at this dose when it is applied intraperitoneally.

The action of pGlu-Amph is modelled on that of the amphetamine, as for the intraperitoneal route, except for the variation in the dose.

On the contrary, pGlu-His-Amph, in the doses being used, always causes a hypothermia followed by a hyperthermia proportional to the administered dose. The maximum of the hypothermia is observed after 2 hours (instead of 1 hour with intraperitoneal administration). The maximum of the hyperthermia is obtained after 3 to 5 hours.

By contrast with the intraperitoneal administration, pGlu-His-Pro-Amph does not exert any action at the administered doses, at least during the first 3 hours. A slight hyperthermia is observed, which is proportional to the administered dose 5 hours after administration.

B—Induction of stereotype movements (1) By intraperitoneal route

Amphetamine causes stereotype movements, of which the intensity and the duration are proportional to the injected dose. With a dosage of 10 mg/kg, where the maximum amplitude of these stereotype movements is achieved, the duration of the effect does not exceed 5 hours.

pGlu-Amph exerts an action which is completely identical with that of amphetamine as regards intensity and duration. By transforming the dose of pGlu-Amph into amphetamine dosage contained in this product, an effect is obtained which is almost identical or is slightly smaller than that which is produced by the equivalent amphetamine dose.

pGlu-His-Amph also causes stereotypes; however, for an equal intensity, the duration thereof is considerably increased by comparison with the duration of those caused by amphetamine (it exceeds 7 hours at the strongest dosage). The dosages of amphetamine contained in pGlu-His-Amph are three times greater than the dosages of amphetamine causing an equal intensity of stereotypes.

The action of pGlu-His-Pro-Amph approaches that of pGlu-His-Amph, but the dosages producing the same effect as the amphetamine are smaller than for pGlu-His-Amph.

(2) Oral route

By the oral route and for an equal dosage, amphetamine exerts an action of less significant intensity and of slightly longer duration than by the intraperitoneal route.

pGlu-Amph produces an effect similar to that of amphetamine. Yet once again, the doses causing an effect similar to that of amphetamine are practically equivalent.

The duration of the stereotyped movements caused by pGlu-His-Amph is considerable: it reaches 27½ hours. A like dose applied perorally causes a much greater effect as regards intensity and duration than when applied intraperitoneally, although the action takes longer to appear (about 3 hours).

With pGlu-His-Pro-Amph, stereotyped movements of low intensity appear in a fairly rapid fashion (between the 30th and 40th minute). After three hours, the effect decreases slightly and then a second phase of greater intensity is observed, which is extended beyond the 7th hour for the dosage of 100 mg/kg. The dosages are higher than the dosages of amphetamine producing an equivalent effect. For an equal dose, the effect is much greater by oral administration than by intraperitoneal administration.

C—Toxicity (1) Intraperitoneal route

Amphetamine and pGlu-Amph have a behaviour which is in fact identical. With toxic dosages, a general syndrome of excitation is observed, with agitation, cries, sweating, jerking, struggling. The dosage of pGlu-Amph causing mortality of 50% is about 40 mg/kg (amphetamine has an $LD_{50}$ which is in the region betweeN 40 and 80 mg/kg).

pGlu-His-Amph, in the dose of 400 mg/kg, causes an agitation which is established after 30 minutes; it follows a sweating phase. The mortality is 10% at this dosage. At 600 mg/kg, 6 mice out of 10 are dead in less than 30 minutes and the agitation is less. At 800 mg/kg, death is immediate (less than 3 min). It follows a few convulsions.

With pGlu-His-Pro-Amph, at 300 mg/kg, death is produced after a variable time (1 hour to 24 hours). It follows signs of excitation, which have been described in respect of amphetamine.

(2) Oral route

With amphetamine and with pGlu-Amph, there are found the same signs of excitation as is the case with the intraperitoneal route, with a slight shift in the toxic dosages: pGlu-Amph, at 30 mg/kg, does not cause any death, whereas a mortality of 100% is observed at 100 mg/kg; the death occurs in 24 to 48 hours.

The toxicity of pGlu-His-Amph, applied orally, is very different from that which is observed when it is applied intraperitoneally. Immediate death is no longer observed, even with the dosage of 2400 mg/kg. Three hours after the administration of the product, stereotypic movements are observed, which last for more than 24 hours. At 2400 mg/kg, 50% of the mice are dead after 2 to 3 days.

With pGlu-His-Pro-Amph, applied orally, it is necessary to reach 1000 mg/kg to observe a mortality of 25% of the mice; the death occurs after 48 hours.

It has to be noted that, by subcutaneous application, TRH at 25 mg/kg potentialises the toxicity of the amphetamine, which changes from the $LD_{50}$ to 17.8 to 5.7 mg/kg.

It is thus noted that the pseudopeptide according to the invention, pGlu-His-Amph, has a toxicity less than that of amphetamine and a much longer lasting action in the test concerning stereotyped movements.

(II) pGlu-His-dopamine pseudopeptides

The chemical structure of pGlu-His-dopamine is directed towards the tests which make evident the central properties of L-DOPA. Dopamine does not pass through the hematoencephalic barrier and the fact of finding, for the pseudopeptide, central properties of L-DOPA type should prove that the peptide fragment imparts original properties to the dopamine, and particularly that of passing through the hematoencephalic barrier.

The different tests which are carried out on mice by the known techniques comprise:
 the action on the rectal temperature of the mouse,
 the anti-reserpine action,
 the potentialisation of the group toxicity to amphetamine,
 the jerking movements with L-DOPA.

(1) Action on the rectal temperature

While confirming the hypothermia conventionally described in respect of L-DOPA, a highly significant hypothermia of precocious occurrence (15 minutes) at relatively high dosage is found in respect of the pseudopeptide.

Dopamine itself also has a hypothermal action, but the amplitude thereof is much smaller.

(2) Interaction with reserpine

L-DOPA in the dosage of 400 mg/kg intraperitoneally antagonises the effects of the reserpine on the temperature and the dropping of the eyelids.

This action is not found with oral administration in the same dosage.

Dopamine has a small effect on the fall in temperature. It completely counteracts ptosis, but the effect is not lasting.

The pseudopeptide, at 400 mg/kg intraperitoneally, slightly counteracts simultaneously the ptosis and the fall in temperature. The duration of this action is short (less than 1½ hours).

(3) Group toxicity in respect of amphetamine

Immediately after the injection of L-DOPA, an extreme agitation of the animals is observed, the said animals becoming aggressive, assuming the stance of a boxer, they cry and jump in the cage. This effect is more developed at 200 mg/kg than at 100 mg/kg.

Dopamine produces a similar effect, but it is only developed about 20 minutes after the injection of amphetamine.

The pseudopeptide causes effects identical with those of dopamine.

The dosage which cause 50% mortality of the animals is high (1120 mg/kg).

(4) Jumping effects with L-DOPA

L-DOPA (100 mg/kg intraperitoneally) causes, in mice which have received d-amphetamine, the occurrence of numerous jumping actions, which have been counted for 90 minutes.

After injection of dopamine, no jumping effects are produced.

The behaviour of the peptide in this test is the same as with L-DOPA, although the delay in the occurrence of the jumping effects is greater and the total number of jumps recorder is smaller than that with L-DOPA.

The pseudopeptide exerts a central action: the hypothermia, the antireserpine action and the jumping effects with L-DOPA confirm this.

The peripheral properties of dopamine seem to be suppressed.

The action is immediate for certain tests (15 minutes for the hypothermia and the antioxotremorine action) and delayed as regards others (jumping effects with amphetamine).

We claim:

1. Pseudopeptide formed by at least one peptide radical originated from a neuropeptide by removal of one of more of the terminal sequences, connected by a peptide bond to a molecule or to a derivative of a therapeutically active molecule acting on the central nervous system, said neuropeptide being selected from the group consisting of endorphine and neuropeptides having from 2 to 11 amino acid sequences and said therapeutically active molecular being selected from the group consisting of amphetamine (Amph), 4-nitro-amphetamine (Amph-NO2), 4-amino-amphetamine (Amph-NH2), 4-chloroamphetamine (Amph-Cl), N-phthaloyl-4-amino-amphetamine, 3,4-dibenzoxyphenyl ethylamine, phenyl ethylamine (PEA), dopamine, 5-(3-aminopropyliden dibenzo-(a,d)-cycloheptadi-1,4-ene (PDD), 1,3-dihydroxy-7-amino 5-phenyl-1H-benzodiazepine-(1,4)-one-(2) (BD), 20-(3-aminopropyl) 3-phenothiazine (PP), 1,5-dimethyl-2-phenyl-4-amino-3-pyrazolone (AP), 4-ethoxyaniline (PT), 4-phenyl-4-ethoxycarbonyl piperidine (NP), tryptamine (Try-NH2) and 4-amino-barbituric acid (AB).

2. A pseudopeptide formed by at least one peptidic radical selected from the group consisting of pGlu-His originated from TRH, Pro-Leu originated from MIF, and Try-Gly-Gly originated from encephaline, said peptidic radical being connected by a

bond to a therapeutically active molecule acting on the central nervous system selected from the group consisting of amphetamine (Amph), 4-nitro-amphetamine (Amph-NO2), 4-amino-amphetamine (Amph-NH2), 4-chloroamphetamine (Amph-Cl), N-phthaloyl-4-amino-amphetamine, 3,4-dibenzoxyphenyl ethylamine, phenyl ethylamine (PEA), dopamine, 5-(3-aminopropyliden dibenzo-(a,d)-cycloheptadi-1,4-ene (PPD), 1,3-dihydroxy-7-amino 5-phenyl-1H-benzodiazepine-(1,4)-one-(2) (BD), 20-(3-aminopropyl) 3-phenothiazine (PP), 1,5-dimethyl-2-phenyl-4-amino-3-pyrazolone (AP), 4-ethoxyaniline (PT), 4-phenyl-4-ethoxycarbonyl piperidine (NP), tryptamine (Try-NH2) and 4-aminobarbituric acid (AB).

3. A pseudopeptide formed by a peptidic radical connected by a peptide bond to a central nervous system acting molecule, said pseudopeptide having central nervous system activity and being selected from the group consisting of pGlu-His-Amph, pGlu His-PEA and pGlu-His-DA.

4. A pseudopeptide formed by a peptidic radical connected by a peptide bond to a central nervous system acting molecule, said pseudopeptide having central nervous system activity and being selected from the group consisting of pGlu-His-Tyr-NH2, pGlu-His-PP, pGlu-His-BD and pGlu-His-PDD.

5. A pseudopeptide formed by a peptidic radical connected by a peptide bond to a central nervous system acting molecule, said pseudopeptide having central nervous system activity and being selected from the group consisting of Pro-Leu-Amph, Pro-Leu-PEA, Pro-Leu-BD, Pro-Leu-PDD and Pro-Leu-PP.

6. Pseudopeptide of a formula of the group consisting of:

pGlu-His-Amph
pGlu-His-PEA
pGlu-His-Amph-Cl
pGlu-His-PEA-di-BzO
pGlu-His-DA
pGlu-His-Amph-NO2
pGlu-His-Amph-NH2
pGlu-His-pNH-Amph-N-Pht
pGlu-His-pNH-Amph
Cbz-Pro-Leu-Amph
Cbz-Pro-Leu-Amph-Cl
Cbz-Pro-Leu-PEA
Cbz-Pro-Leu-Amph-NO2
Cbz-Pro-Leu-PEA-di-BzO
Pro-Leu-Amph
Pro-Leu-Amph-Cl
Pro-Leu-PEA
Pro-Leu-Amph-NO2
Pro-Leu-Amph-NH2
Pro-Leu-DA
pGlu-His-PDD.HCl pGlu-His-BD.HCl
pGlu-His-PP.Hcl
Cbz-Pro-Leu-PDD
Cbz-Pro-Leu-BD
Cbz-Pro-Leu-PP
Pro-Leu-BD
Pro-Leu-PDD
pGlu-His-PT
pGlu-His-AP
Cbz-Pro-Leu-AP
Cbz-Pro-Leu-PT
Cbz-Pro-Leu-NP
Pro-Leu-AP
Pro-Leu-PT
Pro-Leu-NP
N-Cbz-(Bzo)-Tyr-Gly-Gly-PT
N-Cbz-(Bzo)-Tyr-Gly-Gly-AP
Tyr-Gly-Gly-PT
Tyr-Gly-Gly-AP
pGlu-His-Try-$NH_2$
pGlu-His-AB
Cbz-Pro-Leu-Try-$NH_2$
Cbz-Pro-Leu-AB
Pro-Leu-Try-$NH_2$
Pro-Leu-AB.

7. As a novel medicament for asthenia, an effective amount of a pseudopeptide of the class consisting of pGlu-His-Amph and Pro-Leu-Amph together with a pharmaceutically acceptable carrier therefor.

8. As a novel medicament for sympathomimetric action, an effective amount of a pseudopeptide of the class consisting of pGlu-His-PEA and Pro-Leu-PEA together with a pharmaceutically acceptable carrier therefor.

9. As a novel medicament for the treatment of Parkinson's disease, an effective amount of a pseudopeptide of the class consisting of pGlu-His-DA and Pro-Leu-DA together with a pharmaceutically acceptable carrier therefor.

10. As a novel medicament for depletion of serotonin, an effective amount of a pseudopeptide of the class consisting of pGlu-His-Amph-$NO_2$, pGlu-His-Amph-Cl, Pro-Leu-Amph $NO_2$ and Pro-Leu-Amph-Cl together with a pharmaceutically acceptable carrier therefor.

11. As a novel medicament for increase of serotonin, an effective amount of a pseudopeptide of the class consisting of pGlu-His-Amph-$NH_2$ and Pro-Leu-Amph-$NH_2$ together with a pharmaceutically acceptable carrier therefor.

12. As a novel medicament for antidepressive action, an effective amount of a pseudopeptide of the class consisting of pGlu-His-PPD.HCl, and Pro-Leu-PDD, together with a pharmaceutically acceptable carrier therefor.

13. As a novel medicament for tranquilizing effect, an effective amount of a pseudopeptide of the class consisting of pGlu-His-BD.HCl, pGlu-His-PP.HCl, Pro-Leu-BD and Pro-Leu-PP together with a pharmaceutically acceptable carrier therefor.

14. As a novel medicament for anti-epilepsy activity, an effective amount of a pseudopeptide of the class consisting of pGlu-His-AB and Pro-Leu-AB together with a pharmaceutically acceptable carrier therefor.

15. As a novel medicament for analgesic activity, an effective amount of a pseudopeptide of the class consisting of pGlu-His-PT, Pro-Leu-PT and Pro-Leu-NP together with a pharmaceutically acceptable carrier therefor.

* * * * *

UNITED STATES PATENT AND TRADEMARK OFFICE
CERTIFICATE OF CORRECTION

PATENT NO. : 4,297,346
DATED : October 27, 1981
INVENTOR(S) : Richard Rips and Elisabeth Morier It is certified that error appears in the above-identified patent and that said Letters Patent is hereby corrected as shown below:

Column 1, line 26 - change "peptides" to --tripeptides--.

Column 7, line 27 - change "JECL" to --JEOL--.

Column 10, line 50 - change "<10°C." to "-10°C."

Table III, near top of col. 21
        opposite item 59 - change "MP" to --NP--.
        opposite item 62 - change "AP" to --AB--.

Table III, above middle of page
        opposite items 48, 55 and 56 - change "NaOH" to --MeOH--.

Column 29, line 2 - change "Hcl" to --HCl--.

Signed and Sealed this

Eighteenth Day of March 1986

[SEAL]

Attest:

DONALD J. QUIGG

Attesting Officer        Commissioner of Patents and Trademarks